United States Patent [19]

Cohnen

[11] 4,409,232

[45] Oct. 11, 1983

[54] SUBSTITUTED OXADIAZOLES, METHOD FOR THE PRODUCTION THEREOF, COMPOSITIONS CONTAINING THEM AND METHOD OF USE THEREOF

[75] Inventor: Erich Cohnen, Hamburg, Fed. Rep. of Germany

[73] Assignee: Beiersdorf Aktiengesellschaft, Hamburg, Fed. Rep. of Germany

[21] Appl. No.: 290,952

[22] Filed: Aug. 7, 1981

[30] Foreign Application Priority Data

Aug. 13, 1980 [DE] Fed. Rep. of Germany ....... 3030530

[51] Int. Cl.³ .................. C07D 271/10; A61K 31/41
[52] U.S. Cl. ..................................... 424/272; 548/143
[58] Field of Search ......................... 548/143; 424/272

[56] References Cited

U.S. PATENT DOCUMENTS 2,648,669  8/1953  Roemer et al. .................... 548/133

FOREIGN PATENT DOCUMENTS

| 34276 | 8/1981 | European Pat. Off. . |
| 959191 | 2/1957 | Fed. Rep. of Germany . |
| 2461882 | 7/1975 | Fed. Rep. of Germany . |
| 2811638 | 9/1979 | Fed. Rep. of Germany . |
| 868340 | 7/1961 | France .................. 548/143 |
| 1581394 | 9/1969 | France . |

OTHER PUBLICATIONS

Advances in Heterocyclic Chemistry; vol. 5, pp. 141–143; (1965).

Primary Examiner—Mary C. Lee
Attorney, Agent, or Firm—Jordan B. Bierman; Linda Bierman

[57] ABSTRACT

A compound of the formula

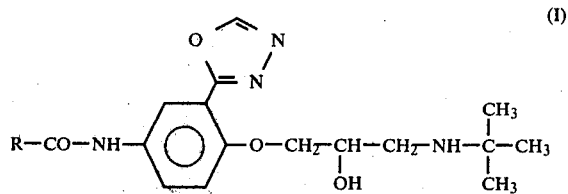

(I)

wherein R is a straight or branched chain alkyl group having 1 to 17 carbon atoms or a cycloalkyl group having 3 to 6 carbon atoms; as well as the physiologically acceptable acid addition salts thereof. A method of production of the compounds, pharmaceutical compositions containing them, and methods of use are also disclosed.

The compounds of the present invention are useful in the treatment of angina pectoris, hypertension, and certain forms of arrhythmia.

12 Claims, No Drawings

SUBSTITUTED OXADIAZOLES, METHOD FOR THE PRODUCTION THEREOF, COMPOSITIONS CONTAINING THEM AND METHOD OF USE THEREOF

This application claims the benefit of the priority of German Application P No. 30 30 530.7, filed Aug. 13, 1980.

The present invention is directed primarily to new oxadiazoles of the formula

Formula I

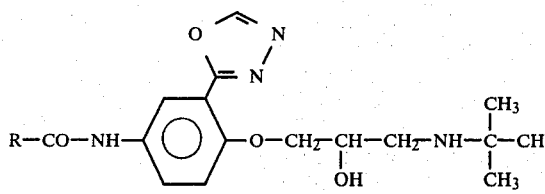

wherein R is a straight or branched chain alkyl group having 1 to 17 carbon atoms, or a cycloalkyl group with 3 to 6 carbon atoms. Also included, are the physiologically acceptable acid addition salts of said compounds, as well as the production thereof, their use in pharmaceutical compositions, and the compositions themselves.

The compounds of the present invention possess superior therapeutic activity, particularly as $\beta_1$-adrenolytic and hypotensive agents. As a result, they are useful in the treatment of angina pectoris, hypertension, and arrhythmia.

R can, with advantage, be methyl, ethyl, n-propyl, isopropyl, n-butyl, sec. butyl, isobutyl, tert. butyl, n-pentyl, isopentyl, neopentyl, amyl, n-hexyl, isohexyl, as well as the branched hexyl groups with a quaternary carbon atom. Also included are the n-, iso-, or quaternary heptyl, octyl, nonyl, decyl groups as well as the corresponding homologues having up to 17 carbon atoms. The n-hexyl group is especially preferred.

R can also be cycloalkyl having 3 to 6 carbon atoms. These constitute cyclopropyl, cyclobutyl, cyclopentyl, and cyclohexyl.

The compounds of the present invention can be administered orally or parenterally. It has been found that a dosage of 0.4 to 5.0 mg/kg (i.v.) lowers isoprenaline-induced tachycardia in rabbits by 50%. The corresponding dosage in man is 50 to 200 mg. per day and is preferably given once or twice daily.

In treating hypertension, it is preferred to administer doses of 50 to 100 mg either once or twice each day. Similarly, treatment of angina pectoris is preferably carried out at a dosage level of 50 to 100 mg twice each day. To control disturbances in heart rhythm, 100 mg are administered once or twice daily.

Most commercial $\beta$-adrenolytics of similar structure influence both $\beta_1$ and $\beta_2$ receptors; that is, they inhibit the effect of the sympathetic nervous system on the heart as well as on the peripheral blood vessels or the bronchial muscles. Blocking of the $\beta_2$ receptors leads to an increase in tonus of the smooth muscle with broncho spasms and increased resistance of the peripheral vessels. The compounds of the present invention, on the other hand, block mainly the $\beta_1$ receptors of the heart. This cardio selectivity is of especially great importance in acute and chronic obstructive bronchial diseases. This is because $\beta_2$ receptor-blocking substances are not to be administered in bronchial diseases (such as asthma) because of their broncho-constrictive action. However, treatment of these diseases with $\beta$-adrenolytics is required.

A further undesired property of many known $\beta$-adrenolytics is their local anesthetic action. This leads to cardio depressive effects or inhibition of heart contraction. The agonistic action component, also known as intrinsic activity (ISA), is similarly an undesirable side effect of many existing $\beta$ blockers. This side effect is of particular disadvantage in the treatment of hypertension. However, the compounds of the present invention are surprisingly superior to the known substances because of the absence of both local anesthetic and agonistic action. Under these circumstances, the extent of the side effects referred to is substantially reduced, minimized, or eliminated.

It is an object of the present invention to provide new compounds which are specifically active on the heart, but are either free from the foregoing undesirable side effects, or exhibit them only to a very minor degree. As a result of the efforts of the Inventor herein, the surprisingly selective and highly active compounds of the present invention have been discovered.

These compounds possess superior properties as compared with other compounds of similar structure. (See German Application No. 28 11 638). It is believed that the specific activities of the present compounds result from the particular structure thereof.

This activity is attributable, among other things, to the ortho position of the 3-tert.-butylamino-2-hydroxy-1-propoxy side chain on the phenyl ring, combined with the acylamino group in the meta position, both relative to the oxadiazole ring. It has also been found that the compounds of the present invention possess a surprisingly long half-life.

Particularly effective and desirable are the compounds of the present invention wherein R contains 1 and 5 to 10 carbon atoms. Salts of these compounds are also to be preferred.

Some of the more desirable and useful compounds are as follows:

(a) 2[2-(2-hydroxy-3-tert.-butylamino-propoxy)-5-acetamidophenyl]-1,3,4-oxadiazole.

(b) 2[2-(2-hydroxy-3-tert.-butylamino-propoxy)-5-n-hexanoylaminophenyl]-1,3,4-oxadiazole.

(c) 2-[2-(2-hydroxy-3-tert.-butylamino-propoxy)-5-n-heptanoylamino-phenyl]-1,3,4-oxadiazole.

(d) 2-[2-(2-hydroxy-3-tert.-butylamino-propoxy)-5-n-octanoylamino-phenyl]-1,3,4-oxadiazole.

(e) 2-[2-(2-hydroxy-3-tert.-butylamino-propoxy)-5-n-nonanoylamino-phenyl]-1,3,4-oxadiazole.

(f) 2-[2-(2-hydroxy-3-tert.-butylamino-propoxy)-5-n-decanoylamino-phenyl]-1,3,4-oxadiazole.

(g) 2-[2-(2-hydroxy-3-tert.-butylamino-propoxy)-5-n-undecanoylamino-phenyl]-1,3,4-oxadiazole.

It has been found that, of the foregoing compounds, (a), (c), (d), (e), and (f) are preferred for their selectivity. Within this group, (c) and (d) have been found to be outstanding. Most preferred is (c) which is both highly selectively active and has a particularly long half-life.

In Table 1, the important pharmacological properties of some of the compounds of the present invention are set forth. In addition, acebutolol and 2-[2-(2-hydroxy-3-tert.-butylaminopropoxy)-phenyl]-1,3,4 oxadiazole are included for comparison with the prior art. The last named compound is disclosed in German Application No. 28 11 638.

TABLE 1

| Ex. No. | R | pA₂ (Atrium) | pA₂ (Trachea) | Cardioselectivity antilog pA₂(A)-Pa₂(T) | ISA % isoprenaline action | Local anesth. action (h) | t₁ |
|---|---|---|---|---|---|---|---|
| 1. | $CH_3$ | 6.68 | 5.38 | 17 | 0 | 0 | 5 |
| 2. | $CH_3(CH_2)_5—$ | 7.3 | 5.9 | 25 | 0 | 0 | 3.5 |
| 4. | $CH_3(CH_2)_6—$ | 7.4 | 5.9 | 32 | 0 | 0 | — |
| 6. | $CH_3(CH_2)_8—$ | 7.1 | 5.8 | 20 | 0 | 0 | — |
| Comparison Substance 1 Acebutolol | | 6.29 | 5.01 | 19 | 27 | present | 1.6 |
| Comparison Subst. 2 2-[2-(2-hydroxy-3-tert.butylaminopropoxy)-phenyl]-1, 3, 4-oxadiazole | | 7.3 | 6.8 | 3 | 79 | 0 | — |

The terms used in Table 1 are defined as follows (from B. J. Clark: "Pharmacology of beta-adrenoceptor blocking agents" in "beta-Adrenoceptor blocking agents", P. R. Saxena and R. P. Forsyth edition.

pA₂ The strength of a beta-adrenoceptor blocker. Corresponds to the negative logarithm of the molar concentration of an antagonist which requires a doubling of the molar concentration of the agonist to achieve a given effect on isolated tissue. As test tissue are used the atrium and trachea of guinea pigs.

Cardioselectivity: antilog pA₂(atrium)-pA₂(trachea)

ISA: "Intrinsic sympathomimetic activity" (beta$_a$-agonistic action). The percent increase of the heart frequency which is induced by a substance, referred to the maximum reaction of isoprenaline (100%). The measurements are carried out on reserpinolized rats which no longer show a sympathic tonus.

t₁₇₈: Time at which the beta-adrenolytic action of a substance in rabbits after i.v. application has decreased to one half.

Table 1 clearly evidences the superior pharmacological activity of the compounds of the present invention. In contrast to Comparison Substance 1, they have no adverse isoprenaline action, while their cardioselectivity is substantially the same or even better. As regards Comparison Substance 2, the compounds of the present invention have outstanding cardioselectivity. In addition, the high isoprenaline action of Comparison Substance 2 is disadvantageous for the reasons previously stated. As can be seen from the Table, the most desirable compound is Example 2, wherein R is n-hexyl, compound (c).

The present invention contemplates the formulation of pharmaceutical compositions which contain, as an active ingredient, a compound of Formula I, or the physiologically and pharmaceutically acceptable salts thereof. The composition may also contain any suitable diluent or vehicle.

As previously indicated, the compounds of the present invention are, with advantage, administered orally or parenterally. They can be provided for oral administration in any of the usual forms, including tablets, dragees, syrups, suspensions, and liquids. For parenteral administration, they may be provided as solutions or suspensions. Of course, they may contain any of the customary additives, adjuvants, disintegration agents, etc. Moreover, the substance being administered may be coated in known manner in order to delay disintegration and resorption in the gastrointestinal tract, thus, extending the activity over a longer period of time.

While the concentration of active ingredient in the finished composition is not particularly critical, it has been found useful to provide 0.1 to 90.0% active agent in the material being administered. It is preferred to maintain a concentration of approximately 1.0 to 90.0%. The solid dosage form is to be preferred, both for manufacture and administration. It has been found useful to prepare the various dosage forms so that each contains 50 to 200 mg of the active ingredient, based upon the preferred daily dose.

The compounds of the present invention are produced by reacting the oxadiazoles of the formula Form. II

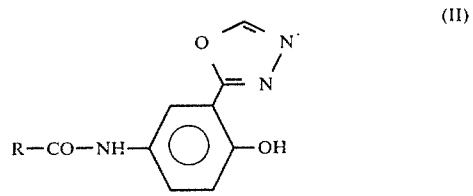

(II)

with epichlorhydrin or epibromhydrin to form a mixture of compounds of the formulas Formulas III & IV pg. 12

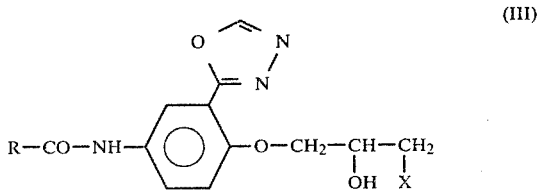

(III)

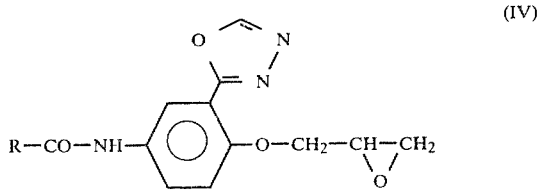

(IV)

wherein X is chlorine or bromine, followed by reaction of such compounds with tert.-butylamine to form the desired end products. The free bases of the present invention may be reacted with acids to form the corresponding acid addition salts. Such reactions are carried out in the usual manner and such acids as hydrochloric, hydrobromic, sulfuric, oxalic, fumaric, or maleic are all suitable. The reaction normally takes place in an alcohol or ether solution.

The compounds of Formula II are produced from the corresponding hydroxybenzoic acid esters:

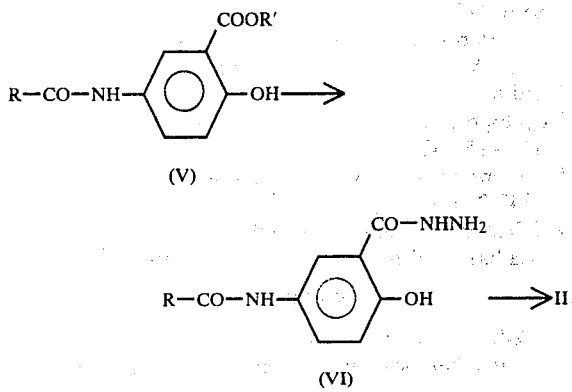

wherein R' is lower alkyl.

A preferred form of the method for the preparation of the compounds of the present invention comprises the following:

(a) reaction of ester V with hydrazine hydrate in methanol or ethanol at boiling temperature to form hydrazide VI.

(b) cyclization of hydrazide VI with ortho-formic acid ester to produce oxadiazole II.

(c) oxadiazole II is reacted with epichlorhydrin or epibromhydrin to form compounds III and IV.

(d) compounds III and IV are reacted with tert.-butylamine to form the desired compounds of Formula I.

Esters V are known in themselves or are available by known methods described in the literature. They can be obtained, for example, by acylation of aminosalicylic acid esters or re-acylation of the known acylamino salicylic acid esters.

The reaction of oxadiazole II with epichlorhydrin or epibromhydrin is preferably carried out at temperatures of 20° to 50° C. The mixture of compounds III and IV (or the individual components after purification) is reacted with the tert.-butylamine at room temperature in the presence of an alcohol solvent.

The following Examples are intended to illustrate the invention:

EXAMPLE 1

2-[2-(2-hydroxy-3-tert.-butylamino-propoxy)-5-acetamido-phenyl]-1,3,4 oxadiazole (a) 41.8 g (0.2 M) 5-acetamido-salicylic acid methyl ester are suspended in 150 ml ethanol and heated to boiling for 4 hours with 12 ml (0.24 M) hydrazine hydrate. After cooling, 24 g of pure hydrazide are isolated by filtering.

(b) 24 g 5-acetamido-salicylic acid hydrazide are heated with reflux for 24 hours with 200 ml ortho-formic acid triethyl ester in 200 ml dimethyl formamide. After distillation of the ortho ester and dimethyl formamide, the residue is admixed with acetone and 14 g of crystalline 2-(2-hydroxy-5-acetamidophenyl)-1,3,4-oxadiazole having a melting point of 235°–236° C. is removed by suction.

(c) 3 g of the oxadiazole of (b) are heated for 12 hours at 50° C. in 30 ml epibromhydrin with addition of 2 drops of piperidine. After separation of the unreacted starting material, the bromhydrin is distilled and the residue triturated with diisopropyl ether. One obtains 0.5 g 2-[2-(2,3-epoxypropoxy)-5-acetamidophenyl]-1,3,4 oxadiazole having a melting point of 173°–175° C.

(d) 0.4 g of compound (c) is stirred in 30 ml methanol and 30 ml tert.butylamine for 15 hours at 20°–25° C. The solvent is evaporated and the residue recrystallized from toluene to yield 0.5 g of 2-[2-(2-hydroxy-3-tert.-butylamino-propoxy)-5-acetamido-phenyl]-1,3,4 oxadiazole having a melting point of 157°–160° C.

(e) If the acid addition salt is desired, 0.4 g of the base are dissolved in ethanol and 65 mg fumaric acid are added. After addition of diisopropyl ether, one obtains 300 mg of the fumarate of 2-[2-(2-hydroxy-3-tert.-butylamino-propoxy)-5-acetamido-phenyl]-1,3,4 oxadiazole having a melting point of 217°–219° C. (decomp.).

EXAMPLE 2

2-[2-(2-hydroxy-3-tert.-butylamino-propoxy)-5-n-heptanoylaminophenyl]-1,3,4 oxadiazole (a) 35 g (0.12 M) 5-n-heptanoylamino-salicylic acid methyl ester are suspended in 200 ml ethanol and heated to boiling for 6 hours with 11.6 ml (0.24 M) hydrazine hydrate. After cooling, 28.2 g of the hydrazide having a melting point of 204°–206° C. are isolated by filtering.

(b) 28 g (0.1 M) of the hydrizide of (a) are heated with 250 ml ortho-formic acid triethyl ester for 3 hours with simultaneous distillation of ethanol. After cooling, 14.1 g of the oxadiazole having a melting point of 207°–209° C. crystallize out.

(c) 1.45 g of the oxadiazole of (b) are dissolved in 50 ml butanone and heated to boiling for 8 hours after addition of 0.7 g potassium carbonate and 0.85 ml epibromhydrin. After separation of the unreacted starting material, the solvent is distilled and the residue purified by HPLC over silica gel. One obtains 0.8 g 2-[2-(2,3-epoxypropoxy)-5-n-heptanoyl-aminophenyl]-1,3,4 oxadiazole having a melting point of 135°–136° C.

(d) 0.7 g of the oxadiazole of (c) are stirred in 20 ml t-butanol and 20 t-butylamine at room temperature for 20 hours. After evaporation of the solvent, the residue is dissolved with a little ethanol and, by addition of oxalic acid (0.12 g), the oxalate of 2-[2-(2-hydroxy-3-tert-.butylaminopropoxy)-5-n-heptanoylamino-phenyl]-1,3,4 oxadiazole is precipitated. The product has a melting point of 152°–153° C. (decomp) and is the oxalate+0.5H$_2$O.

By analogy to Examples 1 and 2, the following compounds of the present invention are obtained:

EXAMPLE 3

2-[2-(2-hydroxy-3-tert.-butylamino-propoxy)-5-n-hexanoylaminophenyl]-1,3,4 oxadiazole M.p. 140°–142° C.

EXAMPLE 4

2-[2-(2-hydroxy-3-tert.-butylamino-propoxy)-5-n-octanoylaminophenyl]-1,3,4 oxadiazole M.p. 182°–183° C. (oxalate+0.5H$_2$O)

EXAMPLE 5

2-[2-(2-hydroxy-3-tert.-butylamino-propoxy)-5-n-nonanoylaminophenyl]-1,3,4 oxadiazole M.p. 130°–132° C.

EXAMPLE 6

2-[2-(2-hydroxy-3-tert.-butylamino-propoxy)-5-n-decanoylamino-phenyl]-1,3,4 oxadiazole M.p. 135°–136° C.

EXAMPLE 7

2-[2-(2-hydroxy-3-tert.-butylamino-propoxy)-5-n-undecanoylaminophenyl]-1,3,4 oxadiazole M.p. 130°–132° C.

The following intermediate substances for the preparation of the compounds of the present invention are prepared in a manner analogous to that set forth in Examples 1 and 2. The starting materials are the corresponding acylamino-salicylic acid esters which are produced by acylation of the amino salicylic acid ester or re-acylation of known acylamino salicyclic acid esters.

5-n-hexanoylamino-salicyclic acid hydrazide M.p. 206°–208° C.
5-n-octanoylamino-salicyclic acid hydrazide M.p. 202°–204° C.
5-n-nonanoylamino-salicyclic acid hydrazide M.p. 204°–206° C.
5-n-decanoylamino-salicyclic acid hydrazide M.p. 203°–205° C.
5-n-undecanoylamino-salicylic acid hydrazide M.p. 205°–206° C.
2-(2-hydroxy-5-n-hexanoylamino-phenyl)-1,3,4 oxadiazole M.p. 210°–211° C.
2(2-hydroxy-5-n-octanoylamino-phenyl)-1,3,4 oxadiazole M.p. 206°–207° C.
2-(2-hydroxy-5-n-nonanoylamino-phenyl)-1,3,4 oxadiazole M.p. 204°–205° C.
2-(2-hydroxy-5-n-decanoylamino-phenyl)-1,3,4 oxadiazole M.p. 204°–207° C.
2-(2-hydroxy-5-n-undecanoylamino-phenyl)-1,3,4 oxadiazole M.p. 206°–208° C.

EXAMPLE 8

2-[2-(2-hydroxy-3-tert.-butylamino-propoxy-5-isobutanoylaminophenyl]-1,3,4 oxadiazole
(R=isopropyl)

(a) 24 g (0.096 M) 5-isobutanoylamino-salicylic acid ethyl ester are suspended in 100 ml ethanol and heated to boiling for 2 hours with 7.3 ml (0.15 M) hydrazinhydrate. After cooling, 21.5 g of the hydrazide having a melting point of 228° C. (decomp) are isolated by filtering.

(b) 20.0 g (0.08 M) 5-isobutanoylamino-salicyclic acid hydrazide are heated under reflux for 5 hours with 100 ml ortho-formic acid triethyl ester and 25 ml dimethyl formamide are added, the resulting ethanol being distilled. After cooling, 12.3 g of the oxadiazole having a melting point of 244°–246° C. crystallize out.

(c) 9.0 g of the oxadiazole of (b) are heated to boiling for 2 hours with 90 ml epichlorhydrin with addition of catalytic quantities of piperidine. After distillation of the excess chlorhydrin and purification of the epoxide by HPLC over silica gel, one obtains, by reaction with tert.-butylamine in tert.-butanol at room temperature and after the usual processing, the oxalate of 2-[2-(2-hydroxy-3-tert.-butylaminopropoxy)-5-isobutanoyl-amino-phenyl]-1,3,4 oxadiazole having a melting point of 178°–183° C.

By analogy to the above examples, the following compounds according to invention were obtained:

EXAMPLE 9

2-[2-(2-hydroxy-3-tert.-butylamino-propoxy)-5-cyclopropanoylamino-phenyl]-1,3,4 oxadiazole
(R=cyclopropyl)

M.p. 115°–117° C.

As intermediate products of the above named compound, there were obtained by analogy to Examples 1, 2 and 8:

5-cyclopropanoylamino-salicylic acid ethyl ester M.p. 154°–158° C.
5-cyclopropanoylamino-salicylic acid hydrazide M.p. 234°–236° C.
2-(2-hydroxy-5-cyclopropanoylamino-phenyl)-1,3,4 oxadiazole M.p. 272°–274° C. (decomp.).

EXAMPLE 10

2-[2-(2-hydroxy-3-tert.-butylamino-propoxy)-5-cyclohexanoylamino-phenyl]-1,3,4 oxadiazole
(R=cyclohexyl), M.p. 110°–114° C.

As intermediate products of the above named compound there were obtained:

5-cyclohexanoylamino-salicylic acid ethyl ester M.p. 184°–186° C.
5-cyclohexanoylamino-salicyclic acid hydrazide M.p. 233°–235° C. (decomp).
2-(2-hydroxy-5-cyclohexanoylamino-phenyl)-1,3,4 oxadiazole M.p. 239°–241° C.

By analogy to the above examples, the following compounds according to invention were synthesized:

| Example | R | M.p. °C. | Salt |
|---|---|---|---|
| 11 | $CH_3CH_2$— | 178–181 | Oxalate + 1 $H_2O$ |
| 12 | $CH_3(CH_2)_3$— | 178–181 | Oxalate + 0.5 $H_2O$ |
| 13 | $CH_3(CH_2)_{10}$ | 126–128 | Base |
| 14 | $CH_3(CH_2)_{16}$ | 124–125 | Base |

The production of drugs using a compound according to the invention is illustrated below:

EXAMPLE 15

Production of tablets

Tablets containing the constituents stated below are produced according to known procedures. They are suitable for the treatment of hypertonia in a dosage quantity of 50 mg once or twice daily, for the treatment of angina pectoris with a quantity of 75 mg twice daily, and for the treatment of forms of arrhythmia (heart rhythm disturbances) using 100 mg once or twice daily.

| Constituents | Weight (mg) Tablet A | Tablet B |
|---|---|---|
| 2-[2-(2-hydroxy-3-tert.-butylamino-propoxy)-5-n-heptanoylamino-phenyl]-1,3,4 oxadiazole | 50 | 75 |
| Tragacanth | 10 | — |
| Lactose | 297.5 | 300 |
| Corn starch | 25 | 15 |
| Talc | 15 | 10 |
| Magnesium stearate | 2.5 | — |

| Constituents | Weight (mg) Tablet A | Tablet B |
|---|---|---|
| | 400 | 400 |

While only a limited number of specific embodiments of the present invention have been expressly disclosed, it is, nonetheless, to be broadly construed and not to be limited except by the character of the claims appended hereto.

I claim:

1. A compound of Formula I

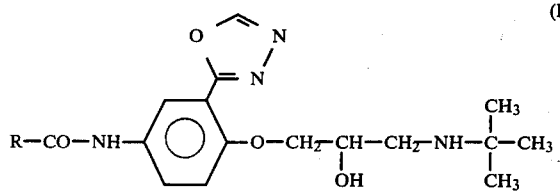

wherein R is a straight or branched chain alkyl group having 1 to 17 carbon atoms or a cycloalkyl group having 3 to 6 carbon atoms, or the physiologically acceptable acid addition salts thereof.

2. A compound of claim 1 wherein R has 1 or 5 to 10 carbon atoms.

3. A compound of claim 1 wherein R is methyl, n-pentyl, n-hexyl, n-heptyl, n-octyl, n-nonyl, or n-decyl.

4. A compound of claim 3 wherein R is methyl, hexyl, heptyl, octyl, nonyl, or decyl.

5. A compound of claim 3 wherein R is hexyl or heptyl.

6. The compound of claim 3 wherein R is hexyl.

7. The compound of claim 3 wherein R is heptyl.

8. The compound of claim 3 wherein R is methyl.

9. A method of treating angina pectoris, hypertension, or arrythmia comprising administering an amount of a compound of claim 1 effective against said angina pectoris, hypertension, or arrythmia, to a warm blooded animal.

10. A method of claim 9 wherein said amount for a human being is 50 to 200 mg per day.

11. A method of claim 10 wherein said amount is administered in two substantially equal doses per day.

12. A method of claim 9 wherein said amount is 100 to 200 mg per day per person.